(12) United States Patent
Yahiro

(10) Patent No.: US 6,182,719 B1
(45) Date of Patent: Feb. 6, 2001

(54) DISTRIBUTION APPARATUS, DISTRIBUTION METHOD AND METHOD OF FITTING DISTRIBUTION TIPS

(75) Inventor: Kanji Yahiro, Fukuoka (JP)

(73) Assignee: Matsushita Electric Industrial Co., Ltd., Kadoma (JP)

( * ) Notice: Under 35 U.S.C. 154(b), the term of this patent shall be extended for 0 days.

(21) Appl. No.: 09/300,919

(22) Filed: Apr. 28, 1999

(30) Foreign Application Priority Data

May 8, 1998 (JP) .................................................. 10-125703

(51) Int. Cl.[7] .................................................. G01N 35/00
(52) U.S. Cl. .............................. 141/130; 141/1; 422/100; 73/864.25
(58) Field of Search ........................ 141/1, 130; 422/100; 73/864.24, 864.25

(56) References Cited

U.S. PATENT DOCUMENTS

| 5,190,727 | * | 3/1993 | Hirsch | 422/100 |
| 5,232,669 | * | 8/1993 | Pardinas | 422/100 |
| 5,827,745 | * | 10/1998 | Astle | 73/864.24 |
| 6,006,800 | * | 12/1999 | Nakano | 141/130 |

* cited by examiner

Primary Examiner—J. Casimer Jacyna
(74) Attorney, Agent, or Firm—Wenderoth, Lind & Ponack, L.L.P.

(57) ABSTRACT

A distribution apparatus for distributing liquid samples using distribution tips, which distribution tips are held in a tip rack placed in a feeder section and fitted relative to a distribution head. The distribution apparatus has a fitting stage, provided in a space between the feeder section and a distribution stage, for supporting the tip rack and fitting the distribution tips. A distribution tip alignment device is provided in the fitting stage, which aligns dislocated distribution tips at the bottom ends to a correct formation by making contact with the side wall surfaces of the distribution tips. The tip ends of the distribution tips, which are attached to nozzles of the distribution head, are aligned by the distribution tip alignment device at a certain specific pitch, at the time when the distribution tips are attached to the nozzles, or after they are attached to the nozzles. By so doing, a liquid sample can be distributed to small diameter wells without having a dislocation problem.

8 Claims, 13 Drawing Sheets

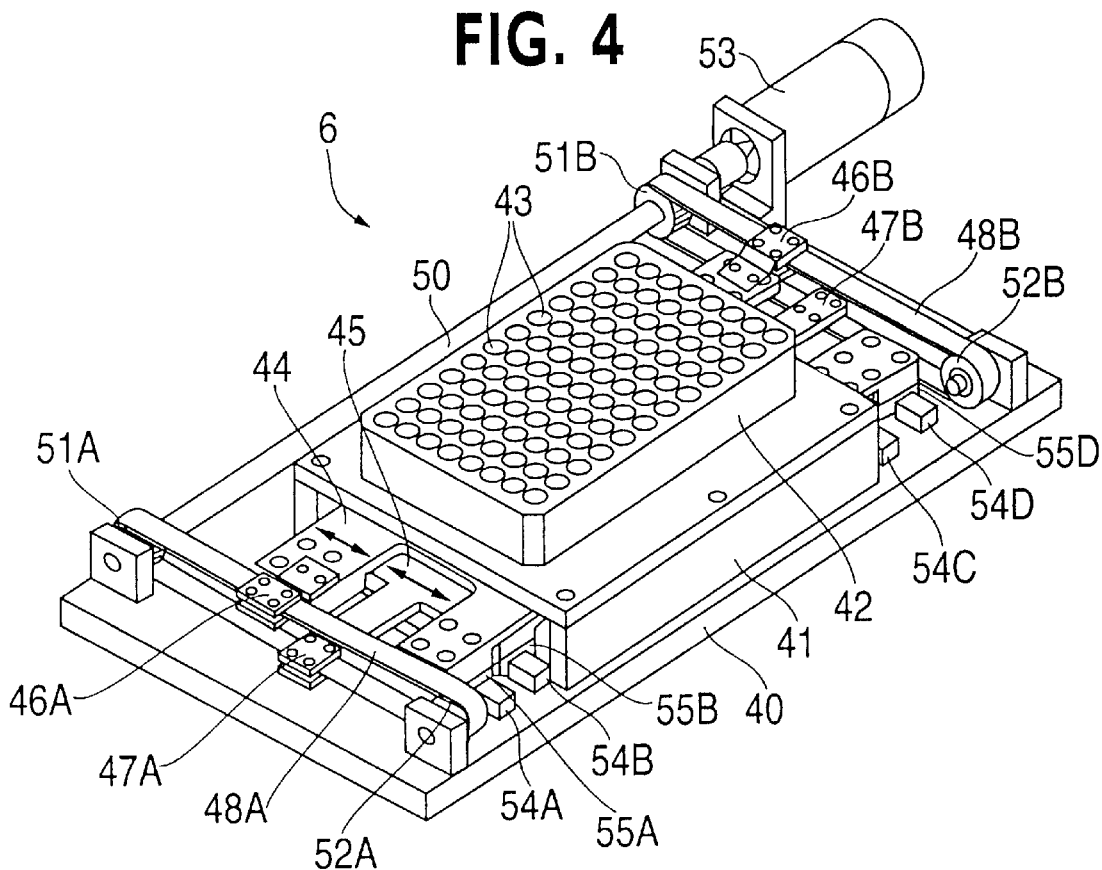

FIG. 9
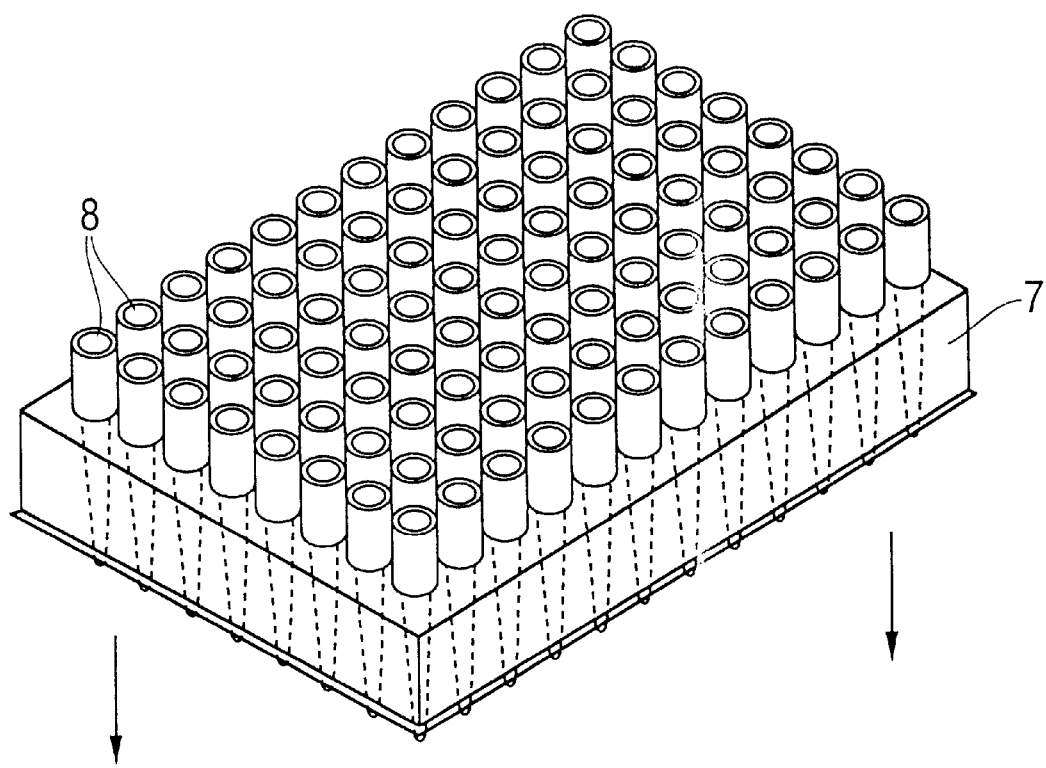
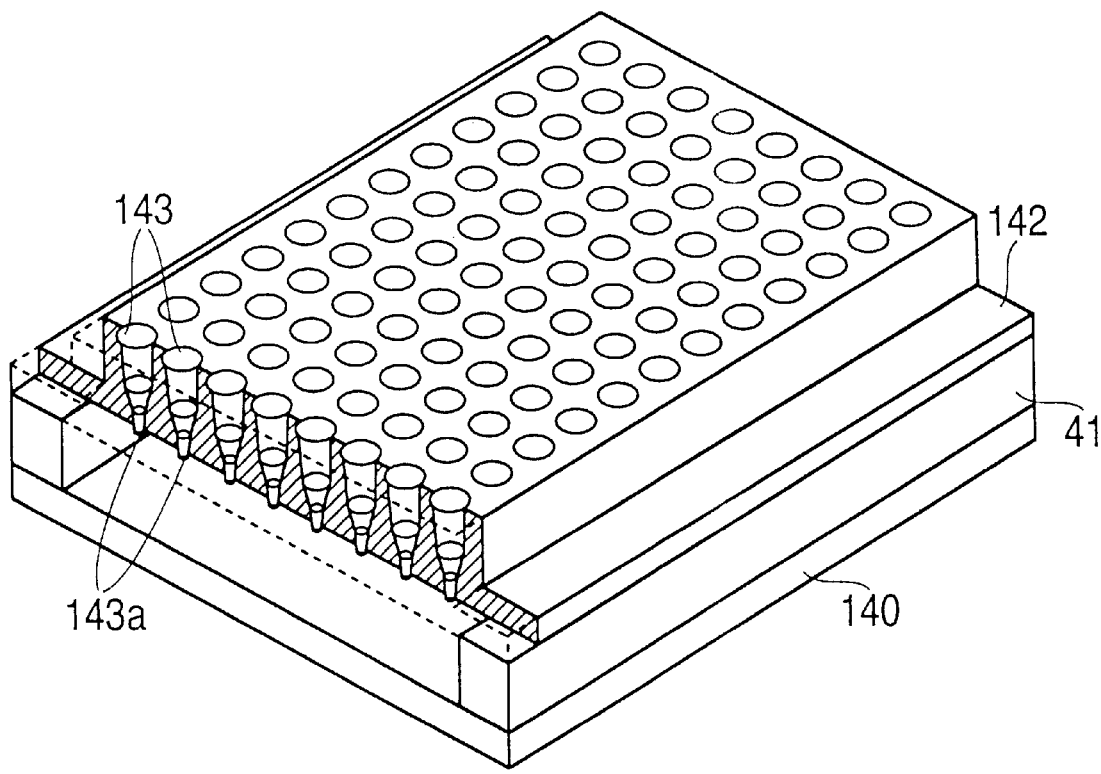

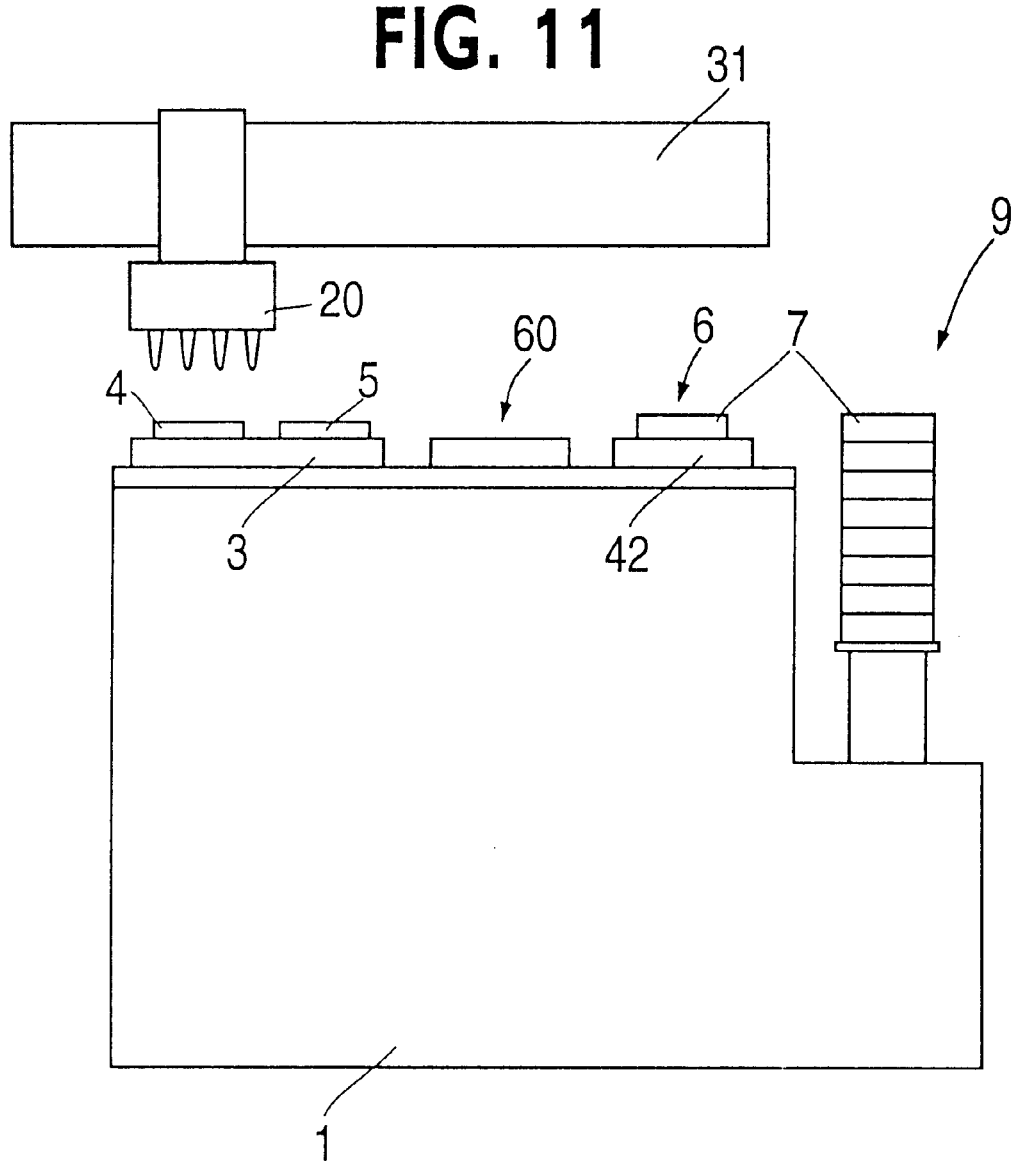

DISTRIBUTION APPARATUS, DISTRIBUTION METHOD AND METHOD OF FITTING DISTRIBUTION TIPS

BACKGROUND OF THE INVENTION

1. Field of the Invention

The present invention relate to a distribution apparatus for distributing liquid samples used in biochemical and the like fields, a method of the distribution and a method of fitting distribution tips.

2. Description of the Related Art

Distributing liquid samples or reagents in small quantities to sample vessels, or a microplate, is a common operation practiced during experimentation or analysis in the biochemical field, for example. The distribution is performed by sucking/discharging a certain liquid using a distribution nozzle. The distribution nozzle is usually fitted with a disposable distribution tip, which is replaced with a new one at any time whenever necessary.

The distribution tip is fitted to the distribution nozzle by inserting the lower end of the latter into a pipet-shaped opening of the distribution tip at the upper end. Fixing of a distribution tip to a distribution nozzle solely depends on the elastic fastening force of an elastic resin-made distribution tip surrounding the lower end of the distribution nozzle. As a result, if an external force is applied to a distribution tip during, or after, a fitting operation, the distribution tip may not be attached straight relative to the distribution nozzle, and the bottom end of the distribution tip will be dislocated. A small amount of dislocation may not cause any material trouble if the diameter of a well in the receiving microplate is sufficiently large. Namely, a small amount of dislocation is acceptable so long as the distribution tip is inserted in the well, and the sucking/discharging of liquid is performed without having any difficulty.

Recently, however, the diameter of wells on a microplate is getting smaller reflecting the general trend of pursuing a higher efficiency in the experimental work and a reduced consumption of samples and reagents. When such a microplate having the small wells is used on a conventional distribution apparatus, the distributing operation may not be performed satisfactorily because of a displaced location of the distribution tip.

The present invention addresses the above problem and offers a distribution apparatus in which the inconveniences stemming from a dislocated distribution tip are curtailed. The methods of distribution, as well as methods of fitting the distribution tip are also offered in the present invention.

SUMMARY OF THE INVENTION

A distribution apparatus for sucking liquid and discharging the liquid into a vessel in accordance with one preferred mode of the present invention comprises a plurality of nozzles, distribution tips to be attached/detached to the lower end of the nozzles, and distribution tip alignment means for aligning the distribution tips relative to a formation.

A method of distributing liquid in accordance with one preferred mode of the present invention comprises the steps of attaching distribution tips to the lower end of a plurality of nozzles, aligning the bottom end of the distribution tips attached to the lower end of the nozzles relative to a formation, and sucking liquid through the aligned distribution tips and discharging the liquid into a vessel.

A method of fitting distribution tips to the lower end of a plurality of nozzles in accordance with one preferred mode of the present invention comprises the steps of provisionally attaching the distribution tips to the plurality of nozzles by inserting the lower end of the nozzles into upper openings of the distribution tips, aligning the provisionally attached distribution tips relative to a formation using the distribution tip alignment means, and attaching the provisionally attached distribution tips completely to the nozzles.

Thus, any displacement of the plurality of distribution tips, which are attached to the lower end of the plurality of nozzles, is corrected by aligning the distribution tips relative to a correct formation by the distribution tip alignment means. Therefore, the distribution of liquid is performed reliably in a normal manner even if the diameter of a well is small.

BRIEF DESCRIPTION OF THE DRAWINGS

FIG. 4 is a perspective view showing distribution tip alignment means in accordance with the first embodiment of the present invention.

FIG. 9 shows perspective views of a fitting stage of a distribution apparatus in accordance with a second embodiment of the present invention.

FIG. 11 is a front elevation view showing a distribution apparatus in accordance with a third embodiment of the present invention.

DETAILED DESCRIPTION OF THE PREFERRED EMBODIMENTS (Embodiment 1)

Figure 1:
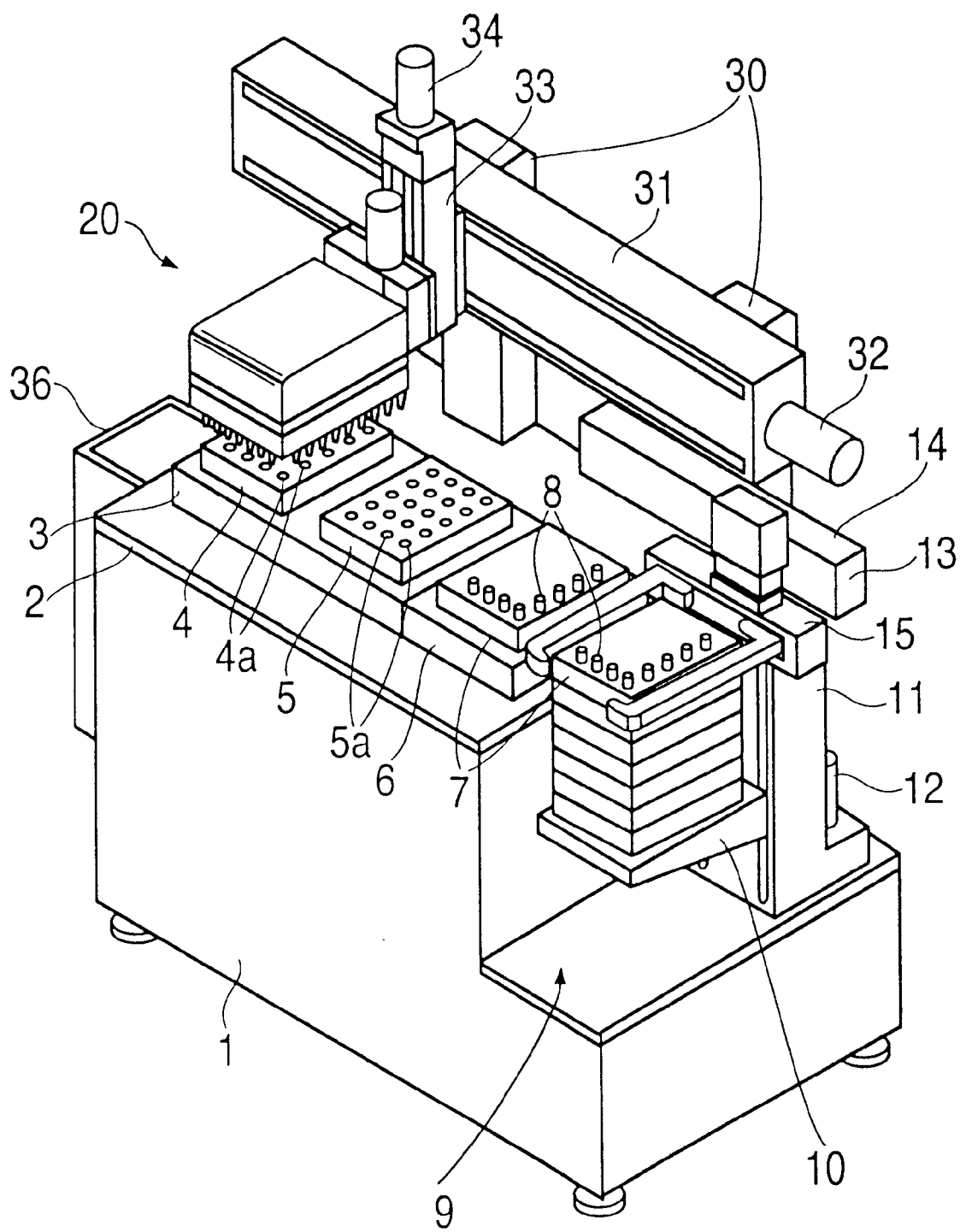
FIG. 1 is a perspective view showing a distribution apparatus in accordance with a first embodiment of the present invention.

The whole structure of a distribution apparatus of a first embodiment is described in the following with reference to FIG. 1. In FIG. 1, a distribution stage 3 is provided on a base plate 2 of a machine bed 1. On the distribution stage 3 are a microplate 4 as a vessel of samples, and a reserver 5. Each of the microplate 4 and the reserver 5 has a number of wells 4a, 5a, respectively, which are hollow for holding the sample liquid. Transferring a reagent kept in the wells 5a of reserver 5 to the wells 4a of microplate 4 using a distribution head 20 (to be described later) performs the distributing operation.

A fitting stage 6 for fitting the distribution tips 8 is provided adjacent to the distribution stage 3. A tip rack is provided on the fitting stage 6, and functions as a holding member for holding a plurality of distribution tips 8. The distribution tip 8 is attached to the distribution nozzle by lowering the distribution head 20 towards the tip rack 7. At a side of the fitting stage 6 is a feeder section 9 of the tip rack 7. The feeder section 9 includes a Z axis table 11 installed vertically on a platform, and the level of the platform is located a step lower than the base plate 2 on the machine bed 1. The Z axis table 11 shifts an elevator table 10 up and down while carrying a stack of tip racks 7.

The feeder section 9 stores a certain number of tip racks 7 stacked on the elevator table 10. A motor 12 of the Z axis table 11 moves the elevator table 10 up and down so as to raise an uppermost tip rack 7 to the same level as that of the tip rack 7 being placed on the fitting stage 6.

A moving table 13 is provided horizontally above the feeder section 9. The moving table 13 is equipped with a cylinder 14, and the cylinder 14 has a chuck 15 provided thereon. The chuck 15 seizes an uppermost tip rack 7 stacked on the elevator table 10 by placing the chuck 15 itself above the feeder section 9, lowering the cylinder 14 and then closing the chuck 15. The cylinder 14 is lifted upward, then the chuck 15 is transferred by the moving table 13 onto the fitting stage 6, the cylinder 14 is lowered again and the chuck 15 is opened. A tip rack 7 is thus transferred onto the fitting stage 6.

A transfer table 31 is horizontally supported by pillars 30 standing on the base plate 2. A Z axis table 33 is provided on the transfer table 31 and is equipped with a Z axis motor 34. A distribution head 20 is installed on the Z axis table 33. The distribution head 20 can move horizontally by operation of the motor 32 on the transfer table 31 such that a range of the movement covers the fitting stage 6, the distribution stage 3 and a discard box 36 provided at a side of the machine bed 1. The distribution head 20 moves vertically by operation of the Z axis motor 34 on the regions of fitting stage 6 and distribution stage 3.

Figure 2:
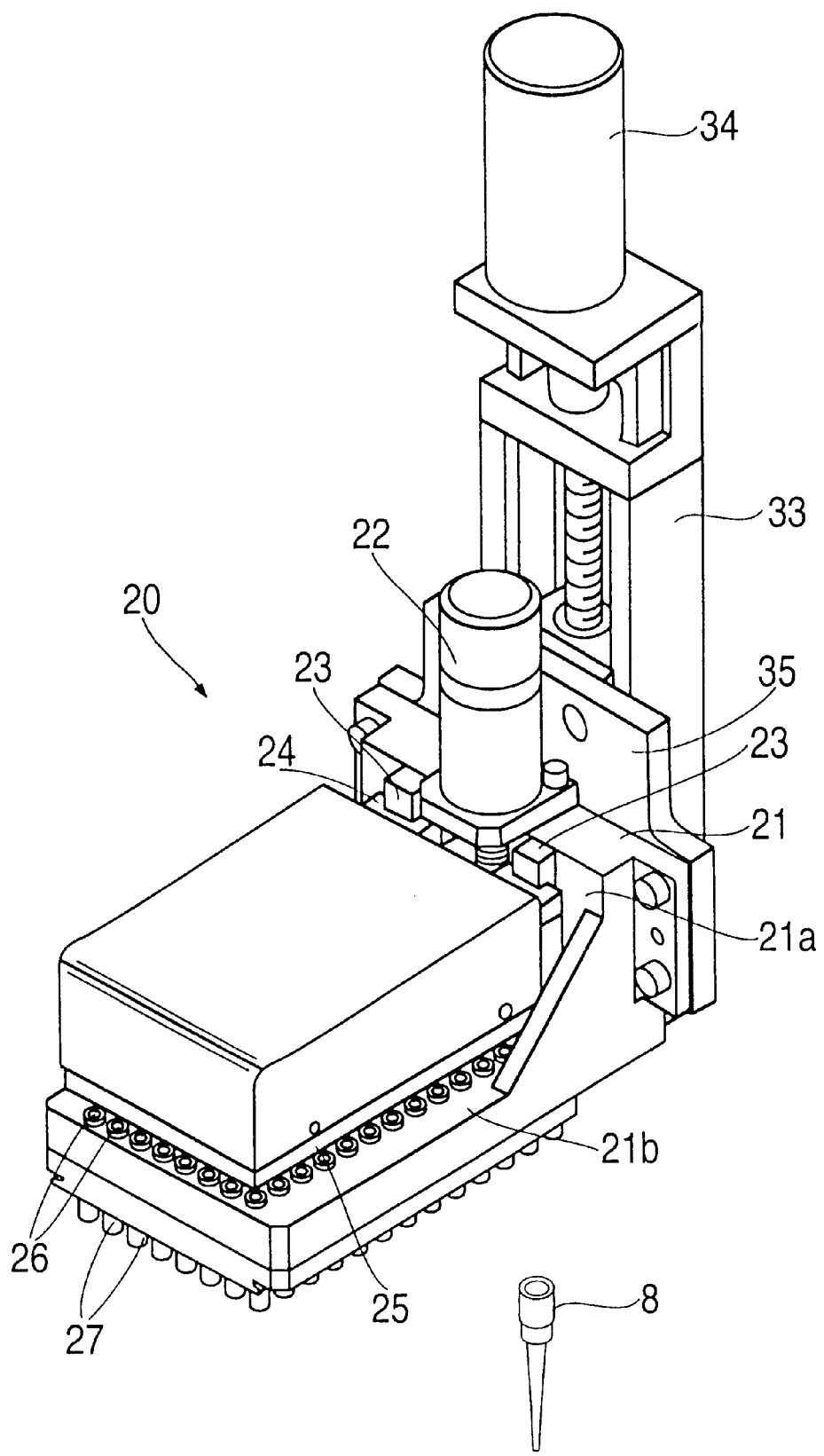
FIG. 2 is a perspective view showing a distribution head in accordance with the first embodiment of the present invention.

The distribution head 20 is described with reference to FIG. 2. As shown in FIG. 2, an "L" shaped block 21 is engaged via a plate 35 with the Z axis table 33. The "L" shaped block 21 is provided with a pair of guide rails 23 vertically disposed on the vertical surface 21a. A slider 24 that is freely slidable with respect to the guide rail 23 is connected with a block 25. The block 25 is equipped with a plurality of plungers 26 arranged in a lattice form. The plungers 26 are engaged with a plurality of nozzles 27, which have been provided in a horizontal plane 21b of the "L" shaped block 21 with the same arrangement as that of the plunger 26.

Now in the following, the operation of the distribution apparatus is described referring to FIG. 1 and FIG. 2. As shown in FIG. 1, the distribution head 20 is shifted to a location on the tip rack 7, precisely aligned relative to the tip rack, and lowered by the operation of Z axis motor 34. The lower ends of the nozzles 27 are inserted in the upper openings of distribution tips 8, which are being held on the tip rack 7, as shown in FIG. 2. When the distribution head 20 is moved upward, the distribution tips 8 are attached to the nozzles 7.

The distribution head 20 carrying the distribution tips 8 is shifted to a place above the reserver 5, and is lowered by operation of the Z axis motor 34 so that the bottom ends of the distribution tips 8 dip into the wells 5a of reserver 5. In this state, the block 25 is raised by operation of a motor 22 end the plungers 26 go up within the nozzles 27. The air within the distribution tips 8 is sucked, and the liquid kept within the wells 5a is sucked up into the distribution tips 8.

Then, the distribution head 20 is shifted to a location above the microplate 4, and is lowered so that the bottom ends of the distribution tips 8 come within the wells 4a of microplate 4. By the operation of the motor 22 the block 25 is lowered, and the plungers 26 move down within the nozzles 27. The liquid that has been sucked and stays within the distribution tips 8 is discharged into the wells 4a through the bottom end of the distribution tips 8.

Figure 3:
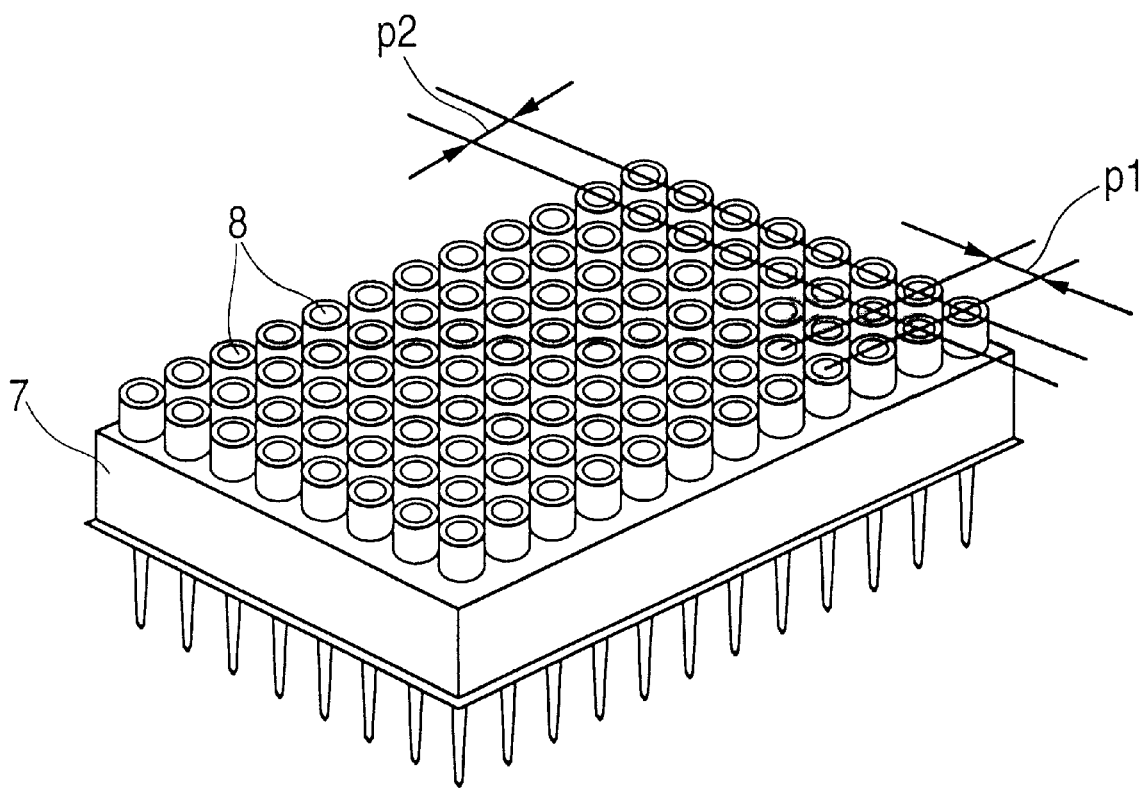
FIG. 3 is a perspective view showing a tip rack in accordance with the first embodiment of the present invention.

Now, the fitting stage 6 and the alignment means for aligning the distribution tips 8 provided in the fitting stage 6 are described with reference to FIG. 3 and FIG. 4. FIG. 3 shows a tip rack 7 used in the distribution apparatus. The tip rack 7 is a box of molded plastic having no bottom plate (see FIG. 7(a)). In the upper plate of tip rack 7 are a number of openings provided in a lattice arrangement with a pitch p1 and a pitch p2. In each of the openings, one of the distribution tips 8 is held in a vertical position. Each tip rack 7 keeps a number of distribution tips 8 in a lattice arrangement (in the present embodiment, 8 pcs.×12 rows=96 pcs.). The tip rack 7 is placed on a fitting stage 6, which is to be described below.

As shown in FIG. 4, a "U" shape supporting frame 41 is provided on the base plate 40, and a fitting section 42 is provided on the supporting frame 41. The outer surface of the fitting section 42 takes a shape that matches the inner surface of the tip rack 7. When a tip rack 7 is placed on the fitting section 42 from above, the tip rack 7 is placed and held at a correct placement with a correct posture. The fitting section 42 is provided with a number of vertical through holes 43 disposed in a lattice arrangement that corresponds to the arrangement of the distribution tips 8 on the tip rack 7. When a tip rack 7 is placed on the fitting section 42, the bottom ends of the distribution tips 8, held on the tip rack 7, extends downward from the fitting section 42 through the vertical through hole 43.

On the base plate 40, located underneath the fitting section 42, four guide rails, 54A, 54B, 54C and 54D, are provided. The respective guide rails 54A, 54B and the guide rails 54C, 54D are disposed close to each other so as to form pairs. The pairs of guide rails are located at both sides of the supporting frame 41 in a symmetrical arrangement. On the guide rails 54A, 54B, 54C and 54D, sliders 55A, 55B, 55C and 55D are engaged, respectively, so as to be freely slidable in a horizontal direction. On the sliders 55A, 55D, a first plate 44 is connected, while on the sliders 55B, 55C a second plate 45 is connected.

A motor 53 is provided at an end portion of the base plate 40. The rotary axis of the motor 53 is connected to a shaft 50. The shaft 50 has pulleys 51A, 51B. Each of the pulleys 51A, 51B is coupled via belts 48A, 48B with the corresponding passive pulleys 52A, 52B. The first plate 44 is connected to the belts 48A, 48B at the upper running portion, via connection members 46A, 46B. The second plate 45 is connected to the belts 48A, 48B at the lower running portion, via connection members 47A, 47B. By the operation of the motor 53, the first plate 44 and the second plate 45 are shifted horizontally by the motion of the belts 48A, 48B, in the direction as indicated with arrow symbols. The shift direction of the first plate 44 and that of the second plate 45 are opposite to each other.

Figure 5A:
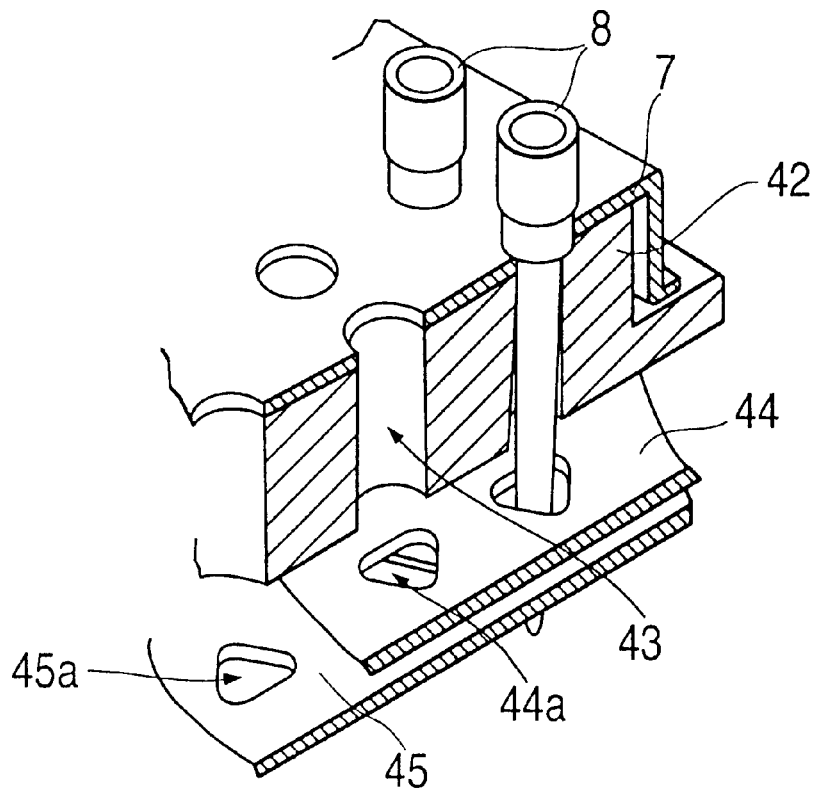
FIG. 5(a) is a partial cross sectional perspective view of the distribution tip alignment means in accordance with the first embodiment of the present invention.

The alignment mechanism for the distribution tips 8 using the first plate 44 and the second plate 45 is described below, referring to FIG. 5 through FIG. 7. FIG. 5(a) shows a state of the tip rack 7 being placed on the fitting section 42. The bottom end of the distribution tips 8 are extending downward through an opening 44a of the first plate 44 and an opening 45a of the second plate 45.

Figure 5B:
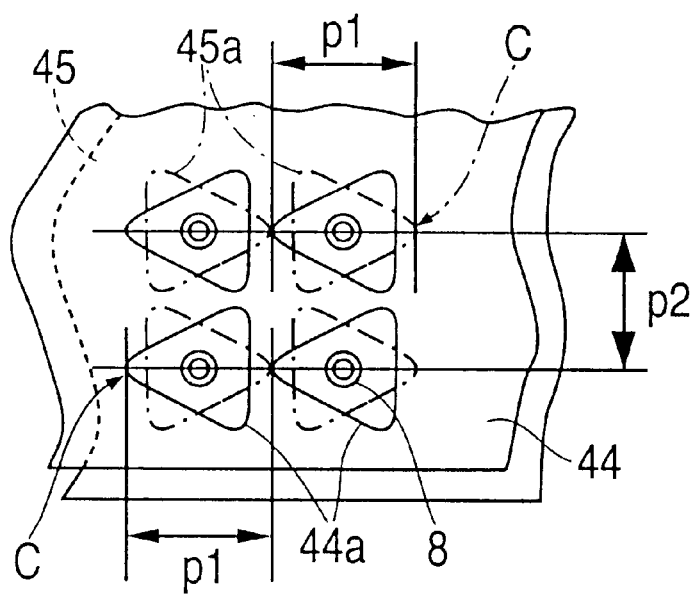
FIG. 5(b) is a plan view of part of the distribution tip alignment means.
Figure 6A:
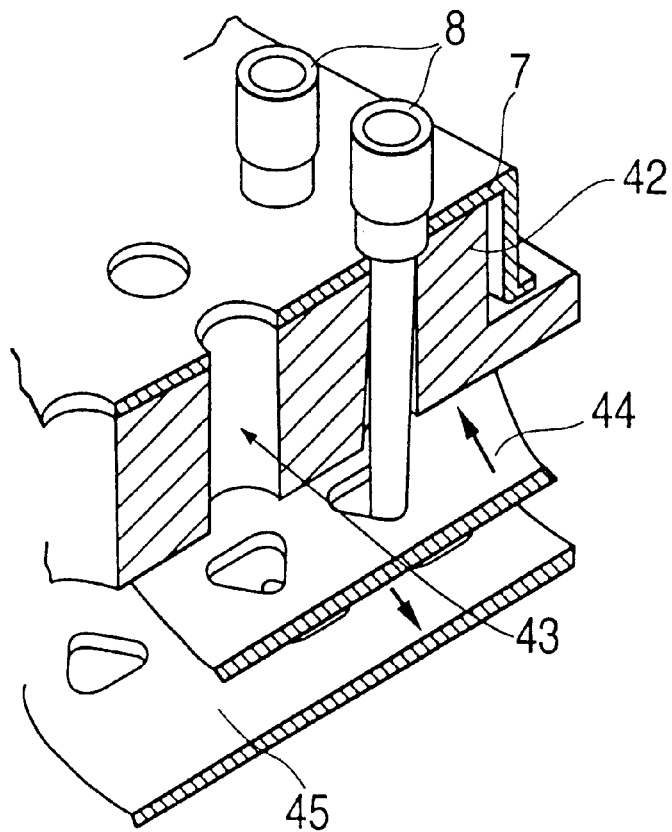
FIG. 6(a) is a partial cross sectional perspective view of the distribution tip alignment means in accordance with the first embodiment of the present invention.

The openings 44a, 45a are described below. As shown in FIG. 5(b), the respective openings 44a, 45a have an approximately triangular shape, with each of the triangles taking a direction opposite to each other. The pitch of arrangement among the respective openings 44a, 45a is identical to that of the tip rack 7, namely, the p1, p2 shown in FIG. 3. The curvature at the summit portion C of the triangles 44a, 45a almost corresponds to the diameter of the outer surface at the bottom portion of each of the distribution tips 8.

When a tip rack 7 is placed, the bottom ends of the distribution tips 8, hanging as it is through the openings 44a, 45a, is not always located at the center of the openings 44a, 45a without having eccentricity. Dislocating in any direction is a rather common situation (see FIG. 7(b)). In order to correct the dislocation and bring the distribution tips 8 into precisely the right alignment, the first plate 44 and the second plate 45 are moved respectively in the directions as indicated with the arrow symbols in FIG. 6(a), by the operation of the motor 53.

Figure 6B:
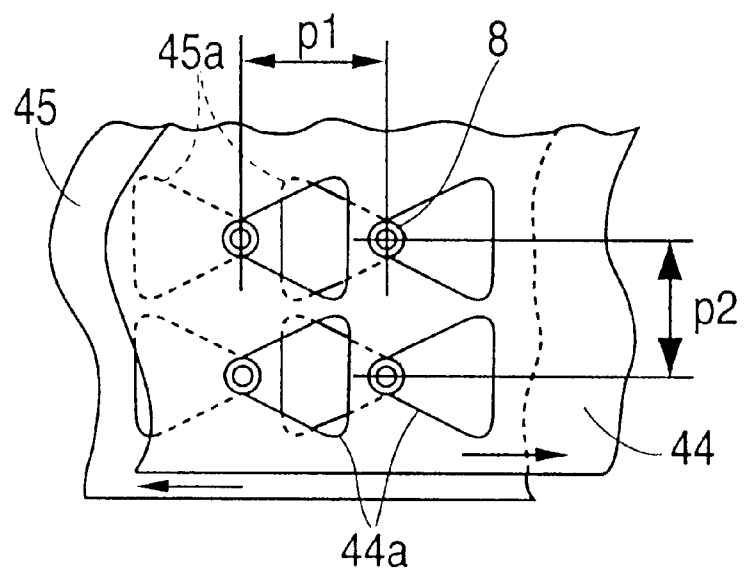
FIG. 6(b) is a plan view of part of the distribution tip alignment means.

As a result of the above operation, each of the openings 44a and 45a move in a direction opposite to each other until the respective summit portions C come into contact with the outer surfaces of the distribution tips 8 at a bottom portion. Thus the distribution tips 8 are pinched by the first plate 44 and the second plate 45. Namely, the first plate 44 and the second plate 45 form a contact member that keeps sidewise contact with the outer surface of the distribution tip 8 at a bottom portion. Under such a state, the distribution tips 8 are held with pitches p1 and p2 in X and Y directions, as shown in FIG. 6(b). In other words, the motor 53, the pulleys 51A, 51B, the belts 48A, 48B, the first plate 44 and the second plate 45 constitute the distribution tip alignment means for aligning the bottom ends of distribution tips 8 which extend downward to a particular formation.

Figure 7A:
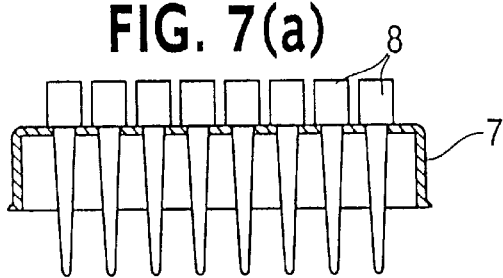
FIG. 7(a)–FIG. 7(d) and FIG. 8(a)–FIG. 8(c) are cross sectional views used to describe a method of fitting the distribution tips in accordance with the first embodiment of the present invention.
Figure 7B:
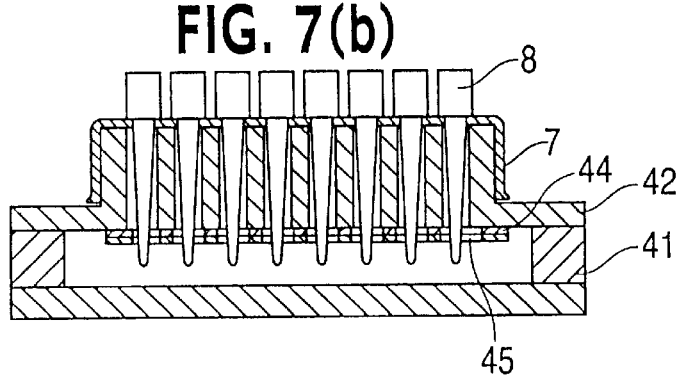
Figure 7C:
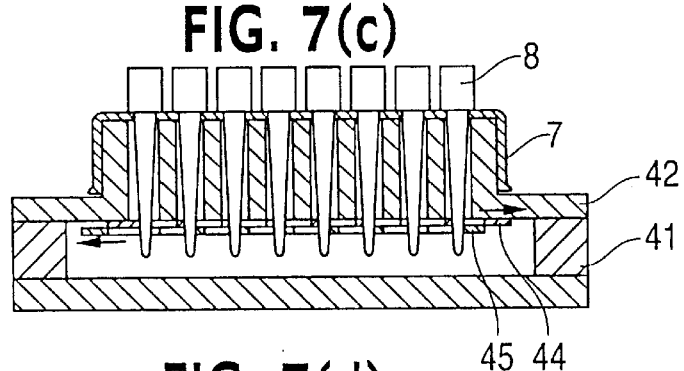
Figure 7D:
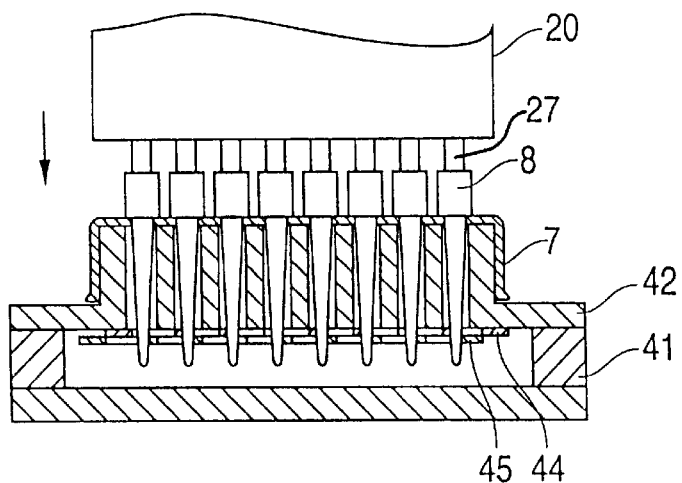

Now the following description is made on a method for fitting the distribution tips using the distribution tip alignment means. FIG. 7 illustrates how the distribution tips 8, which are placed in a tip rack 7, are aligned relative to a correct formation. FIG. 7(a)–FIG. 7(c) show steps of aligning the distribution tips 8. The distribution tips 8 thus aligned are attached to the nozzles 27 by insertion of the lower ends of nozzle 27 into the upper openings of the distribution tips 8, as shown in FIG. 7(d).

Figure 8A:
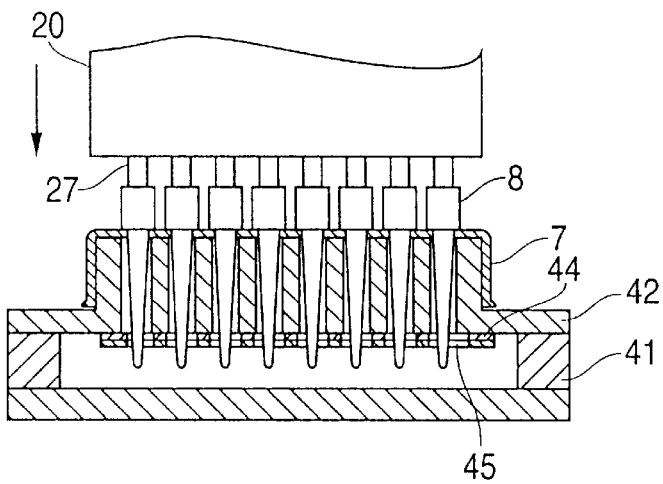
Figure 8B:
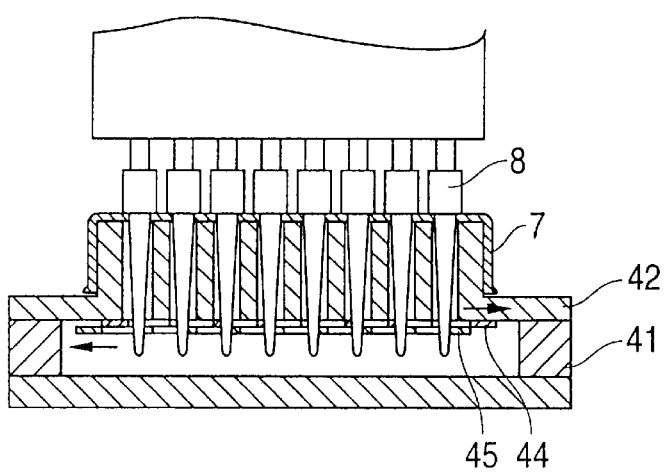
Figure 8C:
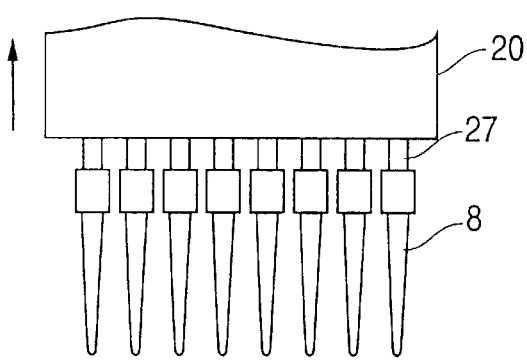

On the other hand, FIG. 8 illustrates a method of aligning the tips into a correct formation after the tips have been attached to the nozzles. As shown in FIG. 8(a), the distribution head 20 is lowered onto the tip rack 7 mounted on the fitting section 42. The lower ends of the nozzles 27 are inserted into the upper openings of the distribution tips 8. And then, as shown in FIG. 8(b), the first plate 44 and the second plate 45 are shifted to align the distribution tips 8 into a correct formation. After that, as shown in FIG. 8(c), the distribution head 20 is lifted up to complete an operation of fitting the distribution tips 8.

Referring to FIG. 8(a), the inserting motion of the lower end of the nozzles 27 may be suspended half way into the upper opening of the distribution tip 8 so as to leave the fitting operation in a provisional state, instead of entirely inserting the tips in a completion of the fitting operation. In this state, the first plate 44 and the second plate 45 are shifted to bring the distribution tips 8 into an aligned formation, and then the distribution head 20 is lowered further to complete the fitting of distribution tips 8 to nozzles 27. Aligning the distribution tips 8 at the provisional fitting state is advantageous in that the amendment of fitting between the nozzle 27 and the distribution tip 8 is easy and that a higher accuracy level is achieved in the alignment.

In accordance with the above-described aligning procedure, a displaced group of distribution tips 8 is aligned into a correct formation by a horizontal force exerted on the outer surfaces at the bottom portions by using the first plate 44 and the second plate 45 as contact members. Thus the fitting between the opening of the distribution tips 8 and the lower ends of nozzles 27 is elaborated to attain a correct state of fitting, and the bottom ends of the distribution tips 8 are lined up precisely with respect to a certain specified formation pitch. In this way, the distribution of liquid is performed precisely without causing any trouble due to displaced distribution tips 8, even to such a microplate 4 whose wells 4a have a small diameter.

(Embodiment 2)

Figure 10A:
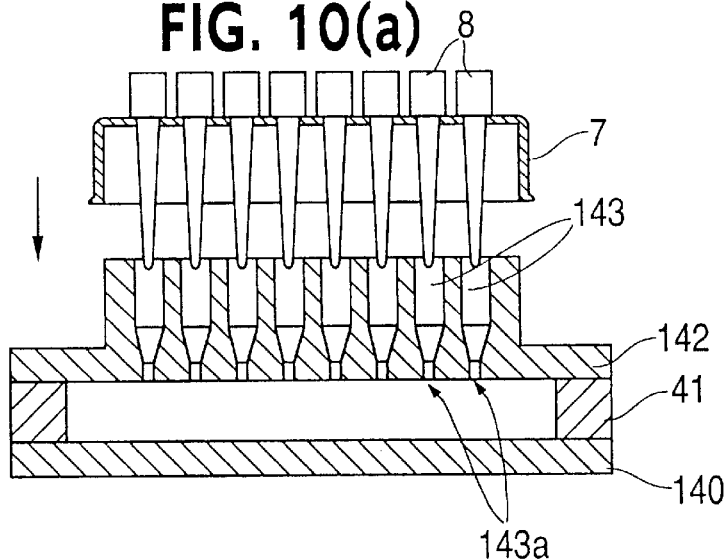
FIG. 10(a)–FIG. 10(c) are cross sectional views used to describe a method of fitting the distribution tips in accordance with the second embodiment of the present invention.
Figure 10B:
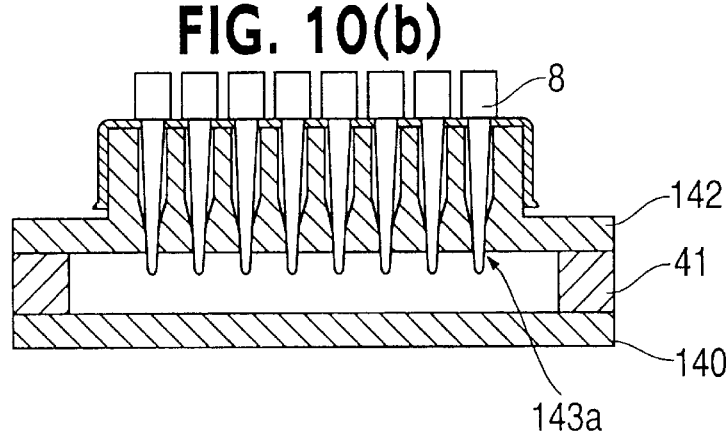
Figure 10C:
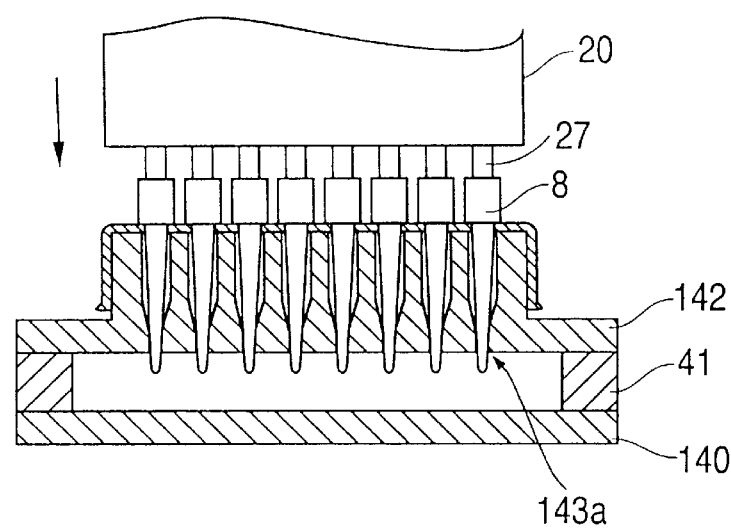

FIG. 9 shows a perspective view of a fitting stage of a distribution apparatus constructed in accordance with a second embodiment of the present invention. FIG. 10(a)–FIG. 10(c) illustrate a method of fitting the distribution tips in accordance with the second embodiment. The point of difference in the present second embodiment as compared with the first embodiment is that the fitting section 42 and the distribution tip alignment means on the fitting stage 6 of the first embodiment have been replaced with a alignment holder 142, which will be described below.

As shown in FIG. 9, the alignment holder 142 is provided on a base plate 140 via a supporting frame 41. Appearance of the alignment holder 142 remains the same as fitting section 42 of the first embodiment, and vertical through holes 143 are provided in a lattice form in the same arrangement corresponding to the holes for distribution tips 8 on the tip rack 7. Each of the vertical through holes 143 has in its lower part a smaller diameter portion 143a (see FIG. 10(a)). The diameter of the smaller diameter portion 143a is approximately identical to the outer diameter of the bottom portion of the distribution tip 8 at a level corresponding to the location of the smaller diameter portion 143a, is in a state of the distribution tips 8 being inserted in the vertical through holes 143.

When a distribution tip 8, held by the tip rack 7, is lowered into a vertical through hole 143, the inner wall surface of smaller diameter portion 143a comes in touch with the outer surface in the bottom portion of the distribution tip 8. As the relative alignment pitch of the smaller diameter portions 143a is identical to a certain specific alignment pitch of the distribution tips 8, the bottom ends of the distribution tips 8 are curbed by the inner wall surface of the smaller diameter portion 143a to provide a certain specific alignment pitch, when a tip rack 7 carrying the distribution tips is mounted on the alignment holder 142. Thus the alignment holder 142 functions as the fitting section for supporting a tip rack 7 as a holding member, and at the same time the inner wall surface of the smaller diameter portion 143a of the alignment holder 142 functions as the contact member making contact at a level lower than the fitting section with the bottom side wall surface of the distribution tip 8 hanging down from the tip rack 7. It further plays the role of distribution tip alignment means for aligning the distribution tips 8.

A method of fitting the distribution tips using the alignment holder 142 is described below with reference to FIG. 10. As shown in FIG. 10(a), a tip rack 7 carrying the distribution tips 8 is mounted on the alignment holder 142, and the bottom end portions of the distribution tips 8 are inserted into the vertical through holes 143. The bottom end portions of the distribution tips 8 proceed along the inner wall surface of the smaller diameter portion 143*a* of the vertical through holes 143, as shown in FIG. 10(*b*), so as to be aligned in the correct formation. In this state, the distribution head 20 is lowered, as shown in FIG. 10(*c*), so that the lower ends of the nozzles 27 move into the upper openings of the distribution tips 8. When the distribution head 20 is lifted up, the distribution tips 8 are attached to the nozzles 27.

As described above, the distribution tips 8 are aligned in a predetermined alignment and kept in the correct positioning before they are attached to the nozzles 27. And then, the distribution tips 8 are attached to the nozzles 27 by inserting the nozzles into the openings of the distribution tips. Therefore, the distribution tips 8 are fitted to the nozzles 27 precisely. Like in the first embodiment, the bottom ends of the distribution tips 8 are kept precisely at a certain specific alignment pitch, and liquid can be distributed without any trouble even to wells having small diameters.

(Embodiment 3)

Figure 12A:
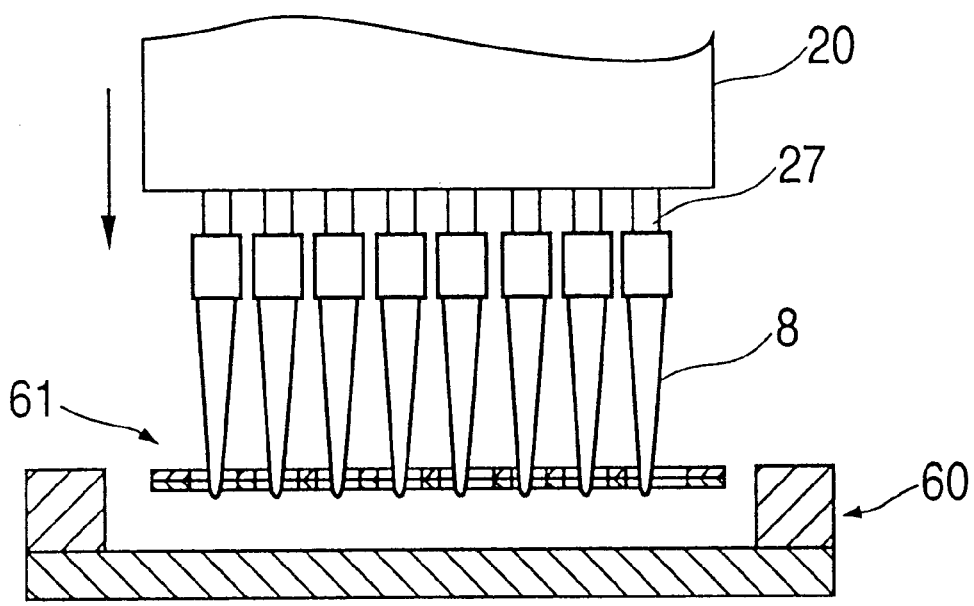
FIG. 12(a)–FIG. 12(b) are cross sectional views showing an aligning section of the distribution apparatus of the third embodiment.
Figure 12B:
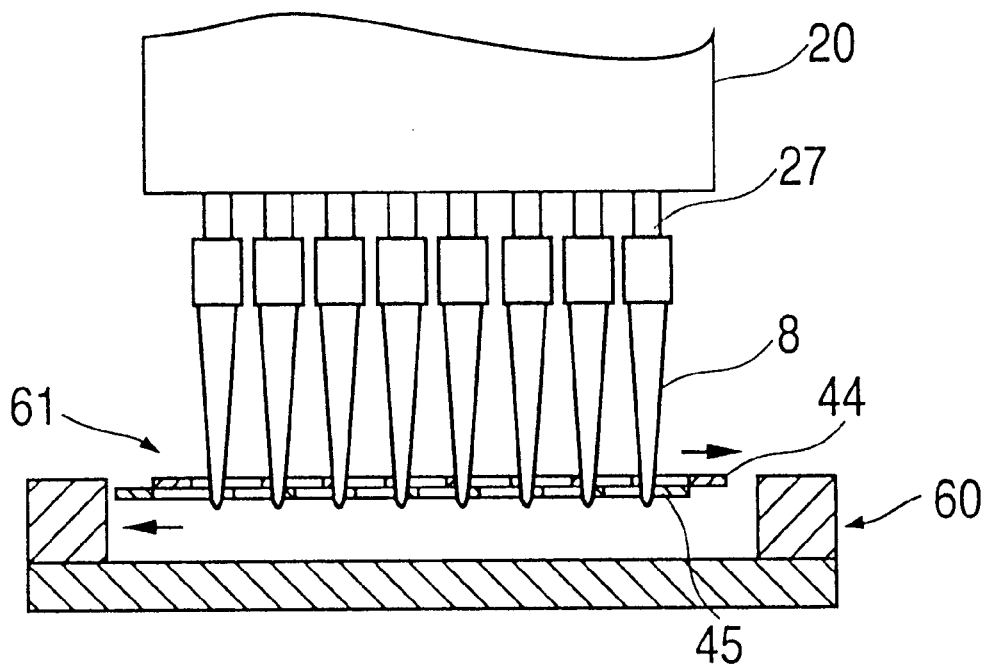

FIG. 11 is a front elevation view of a distribution apparatus constructed in accordance with a third embodiment of the present invention. FIG. 12(*a*), FIG. 12(*b*) and FIG. 13(*a*), FIG. 13(*b*) are cross sectional views of the aligning section of the distribution apparatus. In the first and second embodiments, the distribution tip alignment means included a fitting stage for fitting the distribution tips 8 to the nozzles 27. In the third embodiment, however, the distribution tip alignment means has been separated from the fitting stage, and disposed at a side of the fitting section of the fitting stage.

Referring to FIG. 11, a tip rack feeder section 9, which is identical to that in the first embodiment, is provided on the machine bed 1. A fitting stage 6 for fitting the distribution tips is provided at a side of the feeder section 9. In the fitting stage 6, a fitting section 42 on which a tip rack 7 is mounted, which section is identical to that in the first embodiment, is provided. By lowering the distribution head 20 towards the tip rack 7, the lower ends of the nozzles 27 are fitted with the distribution tips 8. A distribution stage 3, which is identical to that of the first embodiment, is also disposed on the machine bed 1. In a space between the fitting stage 6 and the distribution stage 3, namely at a side of the fitting section 42, a distribution tip alignment section 60 is provided.

The alignment section 60 is described below. As shown in FIG. 12(*a*), a distribution tip aligning device 61 is provided in the alignment section 60. The distribution head 20 carrying the nozzles 27 attached with the distribution tips 8 is lowered towards the alignment section 60 in order to have the distribution tips 8 aligned in a correct formation by the distribution tip aligning device 61. The operating principle of the distribution tip aligning device 61 remains the same as that of the alignment means in the first embodiment, as shown in FIG. 12(*b*), the first plate 44 and the second plate 45 make contact with the side wall surfaces of the bottom portion of the distribution tips 8 for the purpose of locating the distribution tips 8 in a correct position.

Figure 13A:
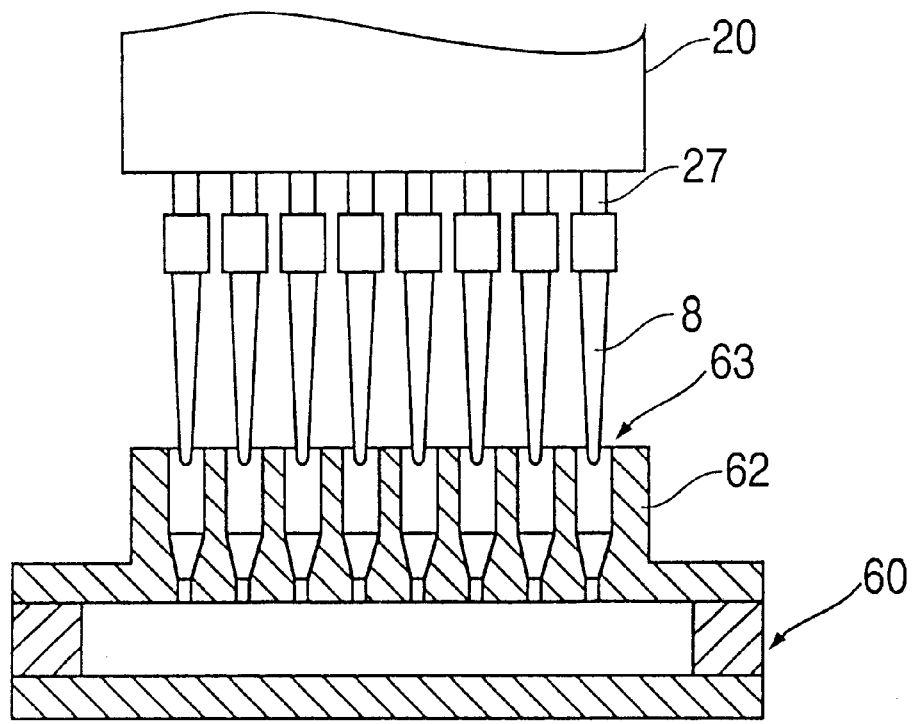
FIG. 13(a)–FIG. 13(b) are other cross sectional views showing an aligning section of the distribution apparatus of the third embodiment.
Figure 13B:
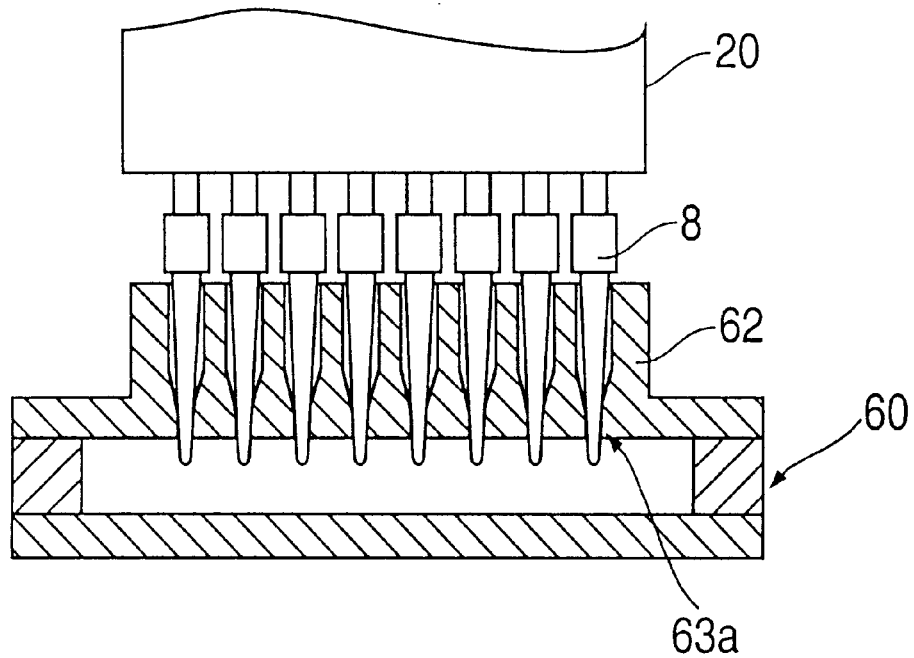

FIG. 13 shows an aligning holder 62 used as a distribution tip alignment means, which is molded and has having the same vertical through holes as those of alignment holder 142 in the second embodiment. Although in the drawing the shape of aligning holder 62 is shown identical to alignment holder 142, the aligning holder 62 may take a kind of block form of a simpler structure, because it is not used for the purpose of fitting section, which supports the tip rack 7.

As illustrated in FIG. 13(*a*), the distribution head 20 carrying the nozzles 27 attached with the distribution tips 8 is lowered towards the alignment section 60 so as to have the bottom ends of the distribution tips 8 inserted in the vertical through holes 63 of aligning holder 62. Displaced distribution tips 8 are curbed by the wall surface of the smaller diameter portion 63*a* of the vertical through holes 63. The side wall surfaces in the bottom portions of the distribution tips 8 keeps contact with the inner wall surface of the small diameter portions 63*a* so as to be curbed or moved to a correct position, as shown in FIG. 13 (*b*). The distribution tips 8 are thus aligned into a correct or desired position.

Although the alignment section 60 and the aligning holder 62, or distribution tip alignment means, have been disposed at a side of the fitting section of fitting stage 6 in the third embodiment, it is not the intention to limit the location of alignment section 60 and aligning holder 62 to the above-described location. These items may be disposed at any location in so far as they are within the reach of the distribution head 20, which moves under the support of the transfer table 31 as shown in FIG. 11. Instead, transfer means may be further provided for moving the alignment section 60 and the aligning holder 62 up and down relative to the distribution head 20 at any desired location of the apparatus.

As described in the foregoing, dislocated distribution tips are moved in the positioning and the bottom ends of the distribution tips are aligned to a correct pitch arrangement by the distribution tip alignment means provided in accordance with the present invention for aligning the distribution tips, which are attached to the lower ends of a plurality of nozzles. In the novel distribution apparatus, liquid can be distributed without experiencing any trouble due to dislocated distribution tips, even when a microplate having small diameter wells is employed.

What is claimed is:

1. A distribution apparatus for sucking liquid and discharging the liquid into a vessel by using distribution tips, said apparatus comprising:
   a holding member for holding the distribution tips;
   a fitting section for supporting said holding member;
   a plurality of nozzles having lower ends capable of attaching to the distribution tips held on said holding member; and
   a distribution tip alignment device for aligning the lower ends of said distribution tips, attached to the lower ends of said nozzles, to a predetermined formation by contacting said distribution tips, wherein said distribution tip alignment device is disposed apart from said holding member.

2. The distribution apparatus as claimed in claim 1, wherein said distribution tip alignment device comprises a contact member that makes contact with side wall surfaces of the distribution tips.

3. The distribution apparatus as claimed in claim 2, wherein said contact member comprises a plurality of holes for receiving said distribution tips, wherein inner wall surfaces of said holes make contact with outer surfaces of the distribution tips, respectively.

4. The distribution apparatus as claimed in claim 3, wherein each of said holes comprises a vertical through hole having a lower part defining a small diameter portion, an upper part defining a large diameter portion, and a tapered portion extending between said large diameter portion and said small diameter portion.

5. The distribution apparatus as claimed in claim 4, wherein said small diameter portion is approximately equal to an outer diameter of a lower section of the distribution tips.

6. The distribution apparatus as claimed in claim 1, wherein said distribution tip alignment device is disposed at a side of said fitting section.

7. A method of distributing liquid, the method comprising:

attaching distribution tips, held on a holding member, to a plurality of nozzles by inserting the nozzles into upper openings of the distribution tips;

aligning the bottom ends of the distribution tips attached to said nozzles with respect to a formation by contacting the distribution tips with a distribution tip alignment means disposed apart from said holding member; and sucking liquid through the aligned distribution tips and discharging the liquid into a vessel.

8. A method of fitting distribution tips to lower ends of a plurality of nozzles, the method comprising:

partially attaching the distribution tips to the plurality of nozzles by inserting the plurality of nozzles into upper openings of the distribution tips;

aligning the lower ends of the partially attached distribution tips, relative to a formation, by contacting the distribution tips with a distribution tip alignment means which is disposed apart from said holding member; and completing the attachment of the aligned distribution tips to the nozzles.

\* \* \* \* \*